United States Patent [19]

Cloyd

[11] 4,159,322
[45] Jun. 26, 1979

[54] ANTICOCCIDIUM IMPLANTS

[75] Inventor: Grover D. Cloyd, Richmond, Va.

[73] Assignee: A. H. Robins Company, Inc., Richmond, Va.

[21] Appl. No.: 919,191

[22] Filed: Jun. 26, 1978

[51] Int. Cl.² .................... A61K 31/71; A61K 31/35
[52] U.S. Cl. ..................................... 424/181; 424/283
[58] Field of Search ..................... 424/181, 19, 283

[56] References Cited
U.S. PATENT DOCUMENTS 3,773,919   11/1973   Boswell .................................. 424/22

OTHER PUBLICATIONS

Mitrovic et al., Chem. Abst., vol. 83, (1975), p. 141,784j.

Primary Examiner—Sam Rosen

[57] ABSTRACT

Subcutaneous anticoccidium implants containing polycyclic ether antibiotic agents to control coccidiosis in warm-blooded animals and method for improving rate of weight gain are disclosed.

14 Claims, No Drawings

ANTICOCCIDIUM IMPLANTS

BACKGROUND OF THE INVENTION

1. FIELD OF THE INVENTION

This invention is concerned with composition and methods for combatting coccidiosis and improving weight gain in warm-blooded animals, having been exposed to or infected with coccidia parasites, by subcutaneous administration of implants which are slow-release forms of certain ionophores, the polycyclic ether antibiotics including salinomycin, 4-methylsalinomycin, monensin, nigercin, grisorixin, disnerycin and lasalocid.

Uncontrolled development of the coccidia parasite in certain warm-blooded animals, excluding man, can debilitate the animal and aggravate other diseases present. Infection with coccidia in one animal can readily be spread throughout the entire group, such as sheep and cattle in the feed lot and pasture, chickens in pens, and canine and feline species of animals through excretion of coccidia oocysts and subsequent ingestion by uninfected animals. According to the present invention, sustained release or small amounts of certain ionophores from an implant administered beneath the skin of warm-blooded animals supplies a steady supply of a small amount of the ionophore to the bloodstream. Transported by the blood to certain coccidia reproduction sites, the ionophores interfere in the life cycle of the parasite, particularly in development of coccidial sporozites, trophozites and immature schizonts. Interference in these stages in the development of coccidia parasites kills a large percentage of these organisms and the number of oocysts excreted is thereby reduced which reduces spread of coccidiosis.

2. DESCRIPTION OF THE PRIOR ART

Subcutaneous implantation of slow release forms of polycyclic ether antibiotics to control coccidiosis in warm-blooded animals has heretofore been unknown. Oral administration of these antibiotics such as salinomycin (U.S. Pat. No. 3,857,948) is used to control coccidiosis in poultry. Slow release forms of drugs and antibiotics for treatment of certain microbial diseases as subcutaneous implants in animals have been disclosed, such as micro-encapsulated biodegradable forms described in U.S. Pat. No. 3,773,919 wherein the matrix for holding medicinals useful as implants is a formulation of polylactide polymer. The coccidia parasite, however, is a class of protozoa living in the cells lining the intestines of animals and control of such parasites in animals via medication absorbed through the blood from a subcutaneous implant was unknown until the present invention.

SUMMARY OF THE INVENTION

The present invention provides novel compositions and methods of controlling and combatting coccidia parasites in warm-blooded animals susceptible to infection and coccidiosis disease. The novel compositions consist of encapsulated polycyclic ether antibiotic suitable for subcutaneous implantation in warm-blooded animals which release the antibiotic through the wall material used for the encapsulation or via biodegradation of the wall material or a combination of both. The implant acts as a reservoir for the anticoccidial agent.

In general, the implants provide a constant supply of anticoccidial agents to the blood of the animals such that the concentration of the agent in the blood is 10 to 200 parts by weight per 100 ml of blood (10–200 nanogram %).

It is therefore an object of the present invention to provide a method for subcutaneously administering anticoccidial agents selected from the polycyclic ether group of antibiotics otherwise known as ionophores to warm-blooded animals in need of treatment, i.e., which are or may become infected with coccidia parasites.

Another object is to provide a method for releasing ionophores as anticoccidial agents to warm-blooded animals in a sustained manner such that the blood level contains 10–200 nanogram % of the agent.

Another object is to provide implant compositions which furnish the means of supplying sustained release anticoccidial agents to the blood stream of warm-blooded animals.

Still another object is to provide a method of increasing rate of weight gain per day of animals used for food.

These and other objects will become apparent to one skilled in the art from a consideration of the following detailed embodiments.

DETAILED DESCRIPTION OF THE INVENTION

The polycyclic ether antibiotic agents useful in this invention are illustrated by the following which are also defined hereby as anticoccidial ionophores: monensin, nigercin, grisorixin, disnerycin, salinomycin, 4-methyl-salinomycin, lasalocid and salts and esters thereof.

The wall materials for encapsulating the foregoing agents may be any material compatible with animal flesh; i.e., non-reactive with animal tissue, in subcutaneous implantation generally of plastic or polymeric nature, such that the agents will diffuse outward from the implant. The implant may take the form of a matrix containing a dispersion of the agent or the form of a capsule having a central reservoir portion containing the agent or a solution of the agent or suspension of the agent. Illustrative of suitable encapsulating or wall materials are those selected from silastic, polyethylene, teflon, polylactides, polylactones, polycarbonates, polymers of p-dioxanone and 1,4-doxepan-2-one and alkyl derivatives thereof, ethyl cellulose, nitrocellulose, cellulose acetate phthalate, shellac, polyacrylic acid, polymethacrylic acid, polyvinylchloride, polyvinyl, butyral, polyvinyl acetate, vinylic copolymers, polystyrene polymethylmethacrylate, maleic anhydride copolymer, alkyl resin, polybasic acid ester of cellulose and the like.

Of the above recited encapsulating materials, silastics, polycarbonates, polylactones, polylactides, p-dioxanone polymers and polyhydric acid esters of cellulose and combinations thereof are preferred.

In general, there is a wide variation in amount of ionophore contained in the encapsulates. For example, small pouches may contain up to 95% by weight of the ionophore and microencapsulates may contain from 5 to 95% by weight ionophore.

The following examples illustrate the compositions and methods of the invention.

EXAMPLE 1

Pouches were made from medical grade MDX (Dow Corning, HH 1398) silastic filled with 1–2 g. salinomycin powder and sealed with medical grade silastic adhesive and cured for 12–24 hours with moist air. Tested for release of salinomycin in saline solution, the pouches released approximately 1–2 mg. salinomycin per week. This release rate is indicative of reasonable expectation that after sterilization by gamma radiation autoclaving or chemical means and implantation subcutaneously in small animals such as sheep and calves infested with or exposed to coccidia parasites, oocyst counts will drop substantially and symptoms of coccidiosis will be absent or negligible. Rate of weight gain increase per day in the feed-lot of about 10% may reasonably be expected due to control of coccidia parasites.

EXAMPLE 2

Although salinomycin is the preferred active ingredient, when in the procedures of Example 1 there are substituted for salinomycin one of the following ionophores, monensin, nigercin, grisorixin, disnercyn, lasalocid, dienamycin, a substantial reduction in oocyst counts in small animals infectable by the coccidia parasite and corresponding increase in weight gain rate will result.

EXAMPLE 3

Larger animals are treated with implants containing the ionophores as prepared by the procedures of Examples 1 and 2, but adjusting for increased amounts of ionophores released, to the size of the animal such that 10–200 nanogram % ionophore is released to the blood. Increased ionophore release is accomplished by
 (a) increasing size of implant (more salinomycin) or
 (b) suspending the ionophore in a liquid carrier such as saline or silicon oil,
 (c) using multiple dosage forms,
 (d) any combination (a), (b) and (c).

Oocyst counts in feces of cattle in feed-lot contaminated with coccidia oocysts can be reasonably expected to be substantially reduced and weight gain increased per day by about 10%.

EXAMPLE 4

Encapsulates of salinomycin or 4-methylsalinomycin are prepared by the procedure of U.S. Pat. No. 3,773,919 as follows: poly-L-lactide, 10.0 g. and salinomycin sodium or 4-methylsalinomycin sodium 1.0 g. were mixed and warmed to the melting point of the lactide. The mixture was cooled and ground into powder. Two grams of the powder injected subcutaneously by syringe into a feed-lot cattle and sheep would expectably reduce oocysts counts and increase weight gain rate.

EXAMPLE 5

Encapsulates of salinomycin are prepared following the procedure of U.S. Pat. No. 3,523,906 as follows: 5 g. of the polycarbonate of 2,2-bis(4-hydroxyphenyl)-propane are dissolved in 50 cc of methylene chloride to prepare a solution. In this solution is dispersed 1 g. of salinomycin. This solution is emulsified to fine droplets in 150 ml of ethylene glycol and the methylene chloride gradually evaporated. The solid microcapsules are collected by centrifuge and rinsed with water. Subcutaneously implanted in feed-lot cattle and sheep or cattle or sheep on pasture, there is expectably obtained reduction in fecal counts of coccidia oocysts and improved weight gain rate.

EXAMPLE 6

Following the procedure of Example 4, but substituting monensin of 4-methylsalinomycin for salinomycin, microcapsules are obtained which give similar results in cattle and sheep as in Example 4.

EXAMPLE 7

The microencapsulates prepared in Example 4, when administered subcutaneously to pigs, can reasonably be expected to increase weight gain rate over controls receiving none by at least 5–10 percent.

EXAMPLE 8

Encapsulates of Example 5, when injected into cats or dogs, can reasonably be expected to reduce infections due to coccidia parasites and the attendant symptoms associated therewith.

Methods of Administration

As stated hereinabove, the implants in the form of encapsulates release ionophore in amount such that the blood contains 10–200 nanogram %. As shown in the examples, various types of encapsulates may be used, all of which may have varying rates of release of the ionophore and, when taken with the variation in sizes of animals, it can be readily realized that varying sizes of implants will be required depending on the situation. In general, however, the size of the implant will vary from about 0.5 to about 4 grams and, if necessary, multiple dosage forms may be administered to large animals such as cattle. The amount of ionophore in the implant may vary from about 5 to 95 wt. %. Encapsulates may be inserted through a slit in the skin or in the case of microcapsules, administered by injection equipment.

Various modifications and equivalents will be apparent to one skilled in the art and may be made in the selection of ionophores and combination thereof and compositions and methods of the present invention without departing from the spirit or scope thereof, and it is therefore understood that the invention is to be limited only by the scope of the appended claims.

What is claimed is:

1. The method of controlling coccidia parasites in warm-blooded animals in need of treatment which consists of administering subcutaneously an implant comprised of an anti-coccidial ionophore selected from the group consisting of monensin, nigercin, grisorixin, disnerycin, salinomycin, 4-methylsalinomycin, lasalocid, salts and esters thereof, said implant supplying an amount of said ionophore to the blood stream of said animal sufficient to interfere with the life cycle of said parasite.

2. The method of claim 1 wherein the implant is an encapsulate of said ionophore.

3. The method of claim 1 wherein said ionophore is embedded in a matrix.

4. The method of claim 1 wherein the animal is a feed-lot ruminant.

5. The method of claim 1 wherein the animal is on pasture.

6. The method of claim 1 wherein the animal is of the canine or feline species.

7. The method of claim 1 wherein the animal is a pig.

8. The method of claim 1 wherein the ionophore is salinomycin.

9. The method of claim 1 wherein the ionophore is 4-methylsalinomycin.

10. The method of claim 1 wherein the ionophore is monensin.

11. A subcutaneous implant for warm-blooded animals comprised of an ionophore selected from the group consisting of monensin, nigercin, grisorixin, disnerycin, salinomycin, 4-methylsalinomycin, lasalocid, salts and esters thereof, said ionophore being present in a form which suitably releases said ionophore to the blood stream of said animal in amount sufficient to combat and control the development of coccidia parasites.

12. The implant of claim 9 wherein the ionophore is salinomycin.

13. The implant of claim 9 wherein the ionophore is 4-methylsalinomycin.

14. The implant of claim 9 wherein the ionophore is monensin.

* * * * *